(12) United States Patent
Koshnitsky et al.

(10) Patent No.: US 7,526,066 B2
(45) Date of Patent: Apr. 28, 2009

(54) RADIATION THERAPY SYSTEM FOR TREATING BREASTS AND EXTREMITIES

(75) Inventors: Jason Koshnitsky, Framingham, MA (US); Alan Sliski, Lincoln, MA (US)

(73) Assignee: Orbital Therapy, LLC, Bedford, MA (US)

( * ) Notice: Subject to any disclaimer, the term of this patent is extended or adjusted under 35 U.S.C. 154(b) by 0 days.

(21) Appl. No.: 11/530,124

(22) Filed: Sep. 8, 2006

(65) Prior Publication Data

US 2007/0211854 A1    Sep. 13, 2007

Related U.S. Application Data

(60) Provisional application No. 60/779,498, filed on Mar. 7, 2006.

(51) Int. Cl.
*G21K 5/08* (2006.01)
*G21K 5/10* (2006.01)

(52) U.S. Cl. .............. 378/68; 378/37; 378/65; 378/203

(58) Field of Classification Search .......... 378/37, 378/65, 68, 69, 196–198, 203, 208; 600/427
See application file for complete search history.

(56) References Cited

U.S. PATENT DOCUMENTS

| | | | | |
|---|---|---|---|---|
| 3,365,575 A | * | 1/1968 | Strax | 378/37 |
| 4,721,856 A | * | 1/1988 | Saotome et al. | 250/583 |
| 5,289,520 A | * | 2/1994 | Pellegrino et al. | 378/37 |
| 5,595,177 A | * | 1/1997 | Mena et al. | 600/429 |
| 5,609,152 A | * | 3/1997 | Pellegrino et al. | 600/429 |
| 5,855,554 A | * | 1/1999 | Schneider et al. | 600/407 |
| 6,298,114 B1 | * | 10/2001 | Yoda | 378/37 |
| 6,463,122 B1 | * | 10/2002 | Moore | 378/65 |
| 6,560,310 B2 | * | 5/2003 | Stark | 378/37 |
| 6,987,831 B2 | * | 1/2006 | Ning | 378/37 |
| 2006/0262898 A1 | * | 11/2006 | Partain et al. | 378/37 |
| 2007/0036267 A1 | * | 2/2007 | Becker et al. | 378/65 |
| 2007/0064867 A1 | * | 3/2007 | Hansen et al. | 378/37 |
| 2007/0242801 A1 | * | 10/2007 | Mackie et al. | 378/65 |

* cited by examiner

*Primary Examiner*—Edward J Glick
*Assistant Examiner*—Thomas R Artman

(57) ABSTRACT

A radiation therapy system optimized for treating extremities such as the breast has unique geometrical features that enable the system to deliver an accurately located prescribed dose to a target volume while eliminating or reducing the collateral dose delivered to the rest of the patient. The patient lies in a prone position on a rotating, shielded table, with the anatomy to be treated protruding through an orifice in the table into the path of a radiation beam. An optional integral imaging system provides accurate target volume localization for each treatment session. Utilizing the effects of gravity on a prone patient maximizes the separation of a target volume within the breast to adjacent critical structures such as the chest wall, heart and lungs, thereby reducing long term complications not associated with the primary disease. A shielded interface surface between the radiation source and the patient reduces patient dose due to scattered or stray radiation. A shielded enclosure for the radiation sources combined with the shielded interface surface eliminates the need for primary shielding in the room and allows the therapy system to be used in a transportable, mobile facility.

6 Claims, 9 Drawing Sheets

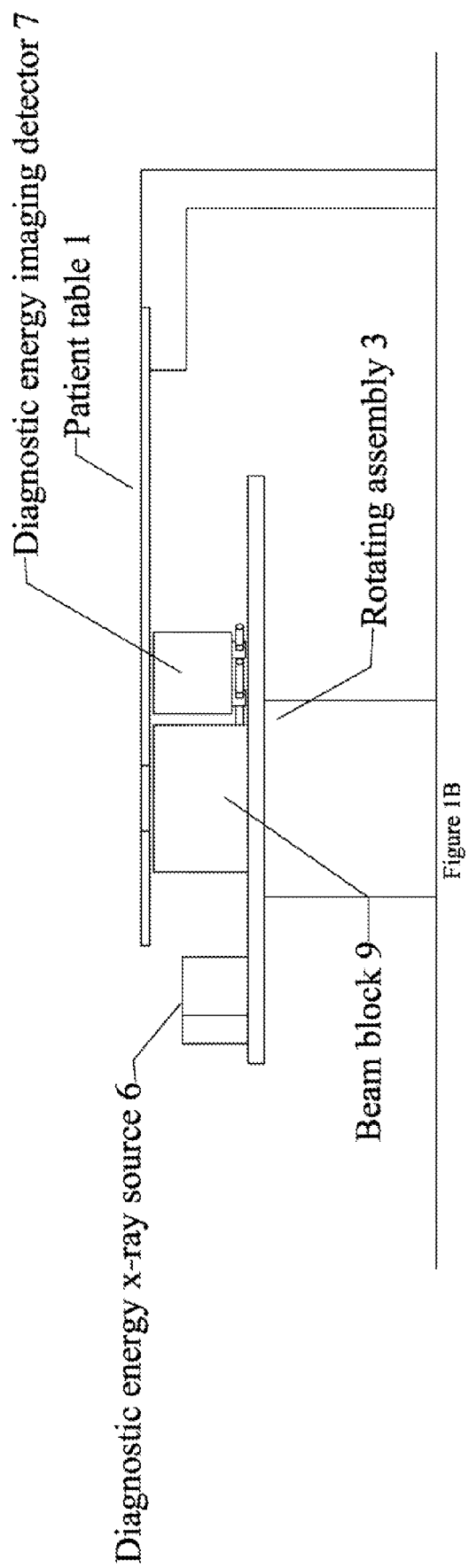

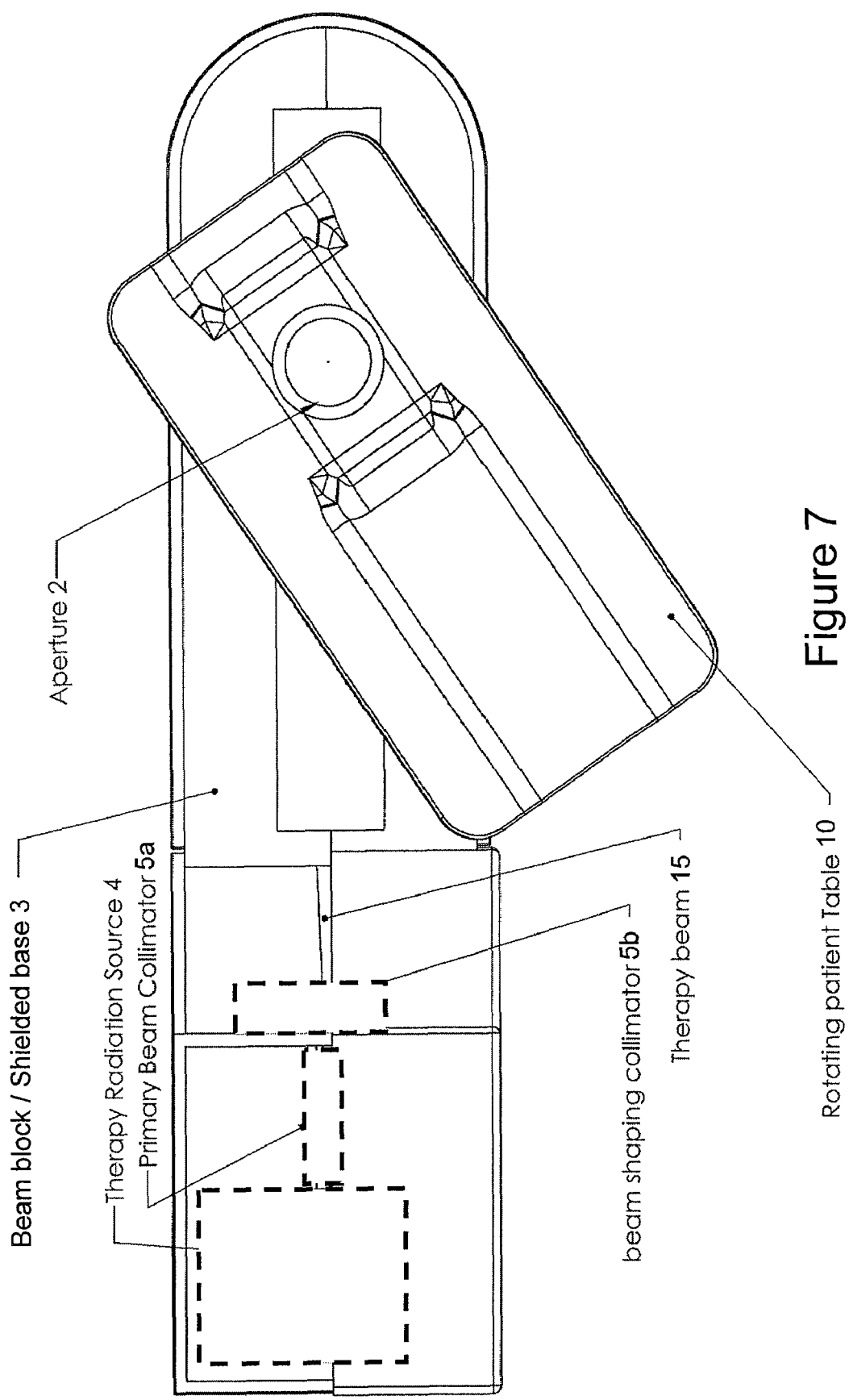

RADIATION THERAPY SYSTEM FOR TREATING BREASTS AND EXTREMITIES

RELATED APPLICATIONS

This application claims the benefit of U.S. Provisional Application No. 60/779,498, filed on Mar. 7, 2006. The entire teachings of the above application are incorporated herein by reference.

BACKGROUND OF THE INVENTION

In order to treat cancer with radiation, it is necessary to deliver the dose prescribed to the target volume, while minimizing the dose to other areas.

Many mechanical configurations of radiation therapy machines and the associated radiation sources have been developed since Roentgen discovered X-Rays. Modern radiation therapy systems use relatively high energy beams of radiation from radioactive isotopes or electron beam X-Ray generators. The X-Ray generators can employ either high voltage direct current or RF driven linear accelerators (LINACs). A mainstream radiation therapy system uses a LINAC to generate an electron beam with between 4 and 22 MeV of energy at low current. The electron beam strikes a high-atomic number target, typically tungsten, and generates penetrating x-rays. The beam is shaped and delivered to the target volume from one or more directions. The overlapping dose at the target volume is generally higher than the dose at the surface from any one delivery angle. The skin is sensitive to radiation, so it is desirable to limit the skin dose to minimize complications. If more fixed beam angles or continuous rotation are used, the surface dose can be spread out more and minimized with respect to the dose delivered to the target volume. It is also desirable to minimize the stray radiation dose to the rest of the patient. Low levels of radiation delivered to a large volume can trigger cancer growth in patients that survive the primary disease for a long time. A significant fraction of all radiation therapy treatments is employed to treat breast cancer with very good success. A typical general purpose radiation therapy system is designed to treat virtually all anatomical sites with some trade-offs being made in the design in order to make a universally applicable machine.

SUMMARY OF THE INVENTION

A machine designed specifically for a limited range of anatomical sites can be designed with different trade-offs to more fully optimize the treatment for a limited range of circumstances.

This invention relates to the optimization of machine and patient positioning geometry to deliver a clinically better treatment for a limited range of anatomical target volumes. By using a novel patient positioner and source geometry, the target anatomy can be separated from the non-target areas of the patient and treated effectively. This invention can be used for many extremities, but for the purposes of illustration of the salient features, and the most probable use of the machine, breast treatments will be discussed.

A substantially horizontal table with an aperture is provided for the patient to lie on in a prone position. The breast to be treated is positioned through the aperture for alignment and treatment. In this position, gravity is an assist in elongating the breast and maximizing the separation between the target volume and the critical structures within the patient such as the chest wall, lung, and heart. By making the table from a shielding material, the unwanted dose from stray radiation to the rest of the patient can be greatly reduced or eliminated.

Any source of radiation can be accommodated as part of this invention, and the energy required to treat small volumes such as the breast or other extremities is lower than a general purpose machine designed to treat target volumes deep in a large patient's abdomen, for example. A compact LINAC, cobalt 60 isotopic source, or ortho- or supervoltage x-ray generator may be employed, depending on the clinician's preference for dose delivery. Lower energy, simpler systems may be preferred in remote areas where maintenance is limited.

The design of the system employs a positionable, rotational element. The radiation source or the patient positioner can be rotated about a substantially vertical axis, the motions being geometrically equivalent. In the case of a configuration employing a rotating radiation source, the rotating element may also include an optional diagnostic energy imaging source and detector system for localizing the target volume in situ at the time of treatment. As can be appreciated by one of skill in the art, a source assembly and associated shielding will typically weigh many times the weight of patient plus patient positioner. The invention can consist of only the patient positioning and radiation source systems, or also employ a diagnostic energy x-ray source and imaging system. If the radiation therapy source can also produce diagnostic energy and quality beams, only one radiation source is required if imaging is desired. The imaging system can be optical or use ionizing radiation. Utilizing a high energy portal imager in the path of the therapy beam after the treated anatomy is also a possible configuration.

The rotational movement combined with an ionizing radiation imaging source and detector can be used to generate plane orthogonal x-rays, cone beam CT, or digitally reconstructed radiographs to assist in anatomical positioning. The position of the anatomy with respect to the radiation beam size, shape, and position can be adjusted to locate the therapy beam in the desired position with respect to the anatomy. Alternatively, the radiation beam size, shape, and or position can be adjusted with respect to the anatomy to provide alignment for the planned treatment.

The rotational movement of the patient positioner or the beam in conjunction with the radiation source and a multileaf collimator or other beam modulation device can be used to deliver a highly optimized, pre-planned dose distribution to the treatment volume.

The gravity assist of a prone patient position and optional anatomy fixation device maximize the separation of the target volume with respect to critical structures and other areas not intended to receive radiation.

By making the patient support table from a shielding material such as lead, and extending the beam block to surround the radiation source(s) entirely, the system can be made self-shielding. General purpose radiation therapy machines that use higher energy beams for treating deep targets in the abdomen, for example, operate at up to and sometimes exceeding 21 MeV. This requires extensive shielding as the primary beam is very penetrating. Above 8 MeV, an x-ray beam produces neutrons which require additional thick shielding. A typical concrete bunker for a LINAC has walls on the order of 4 feet thick, leading to substantial construction costs and a large installation footprint. By optimizing the design of the machine for smaller anatomical targets, the energy of the therapy beam does not need to approach the neutron production threshold, significantly reducing the neutron shielding requirements. A self shielded machine can be installed in a room with minimal shielding, such as employed for CT or diagnostic x-ray rooms. This approach reduces the cost of installation substantially and also makes mobile operation feasible, bringing standard-of-care treatment options to smaller hospitals and rural areas with a low population density.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1B is a side cross-sectional view of the therapy system shown in FIG. 1A.

FIG. 7 is a top plan view of the therapy system shown in FIGS. 5, 6A and 6B.

DETAILED DESCRIPTION OF THE INVENTION

This invention relates to the devices and methods for delivering an accurately located dose of radiation to a predetermined target volume within an anatomical site such as a breast. The following description and figures illustrate both a machine configuration where the patient positioner is non-rotating, and a machine configuration where the patient positioner rotates around a non-rotating radiation source and optional imaging system, which is geometrically equivalent.

Figure 1A:
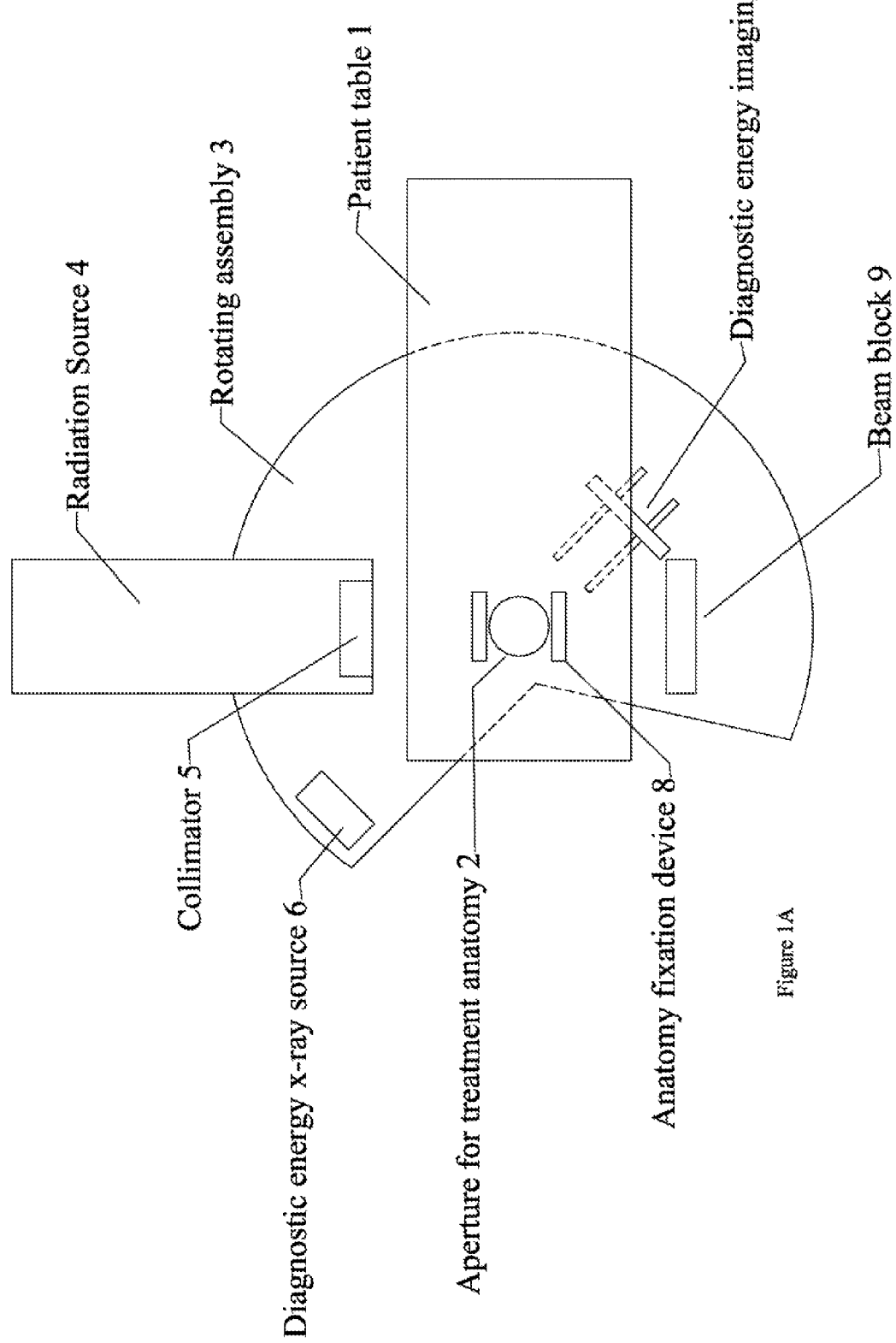
FIG. 1A is a plan cross-sectional view of a therapy system of the present invention.
Figure 2:
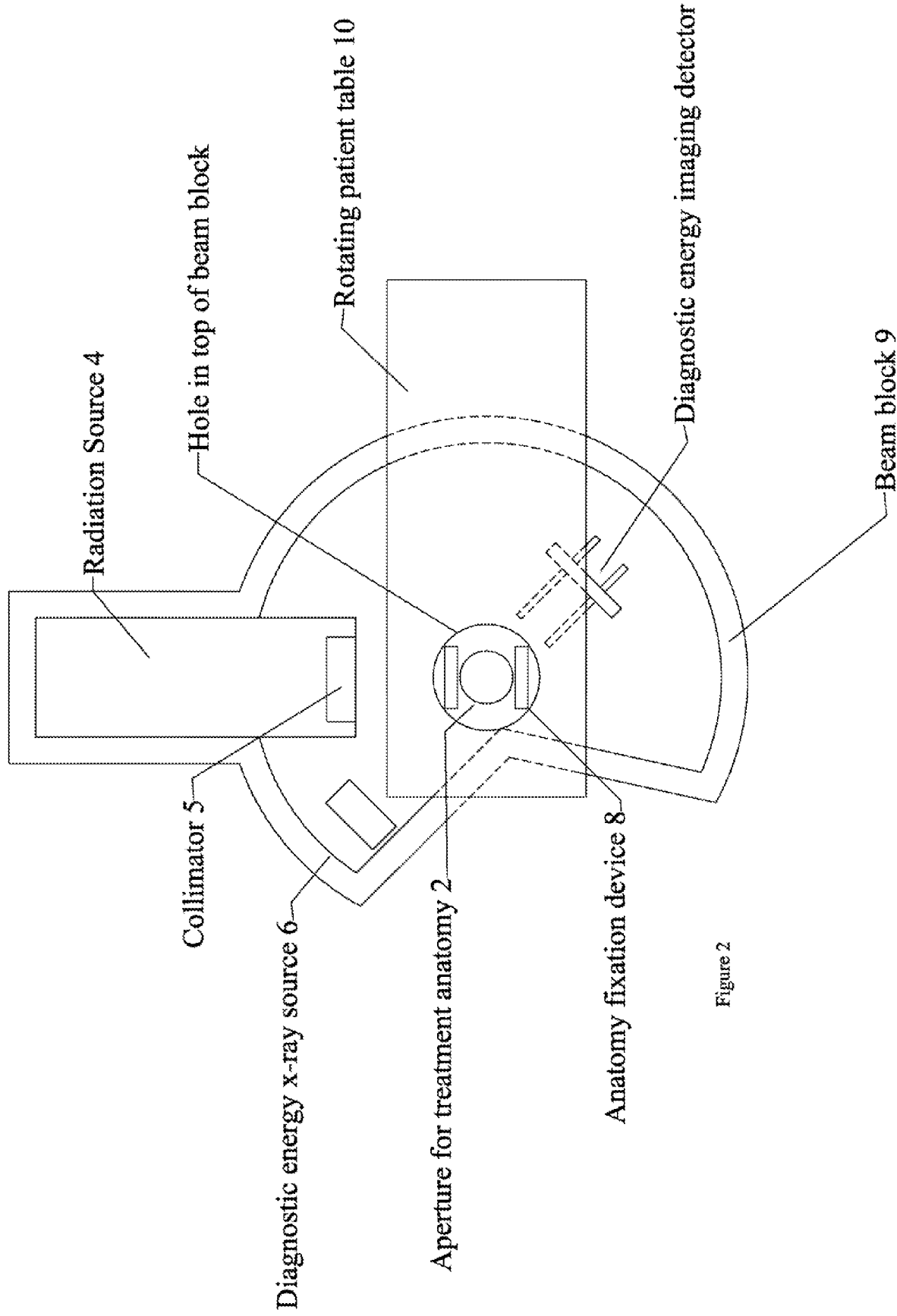
FIG. 2 is an illustration showing a plan cross sectional view of the fully shielded version of the invention with rotating patient table and fixed radiation source and imaging assembly.
Figure 3:
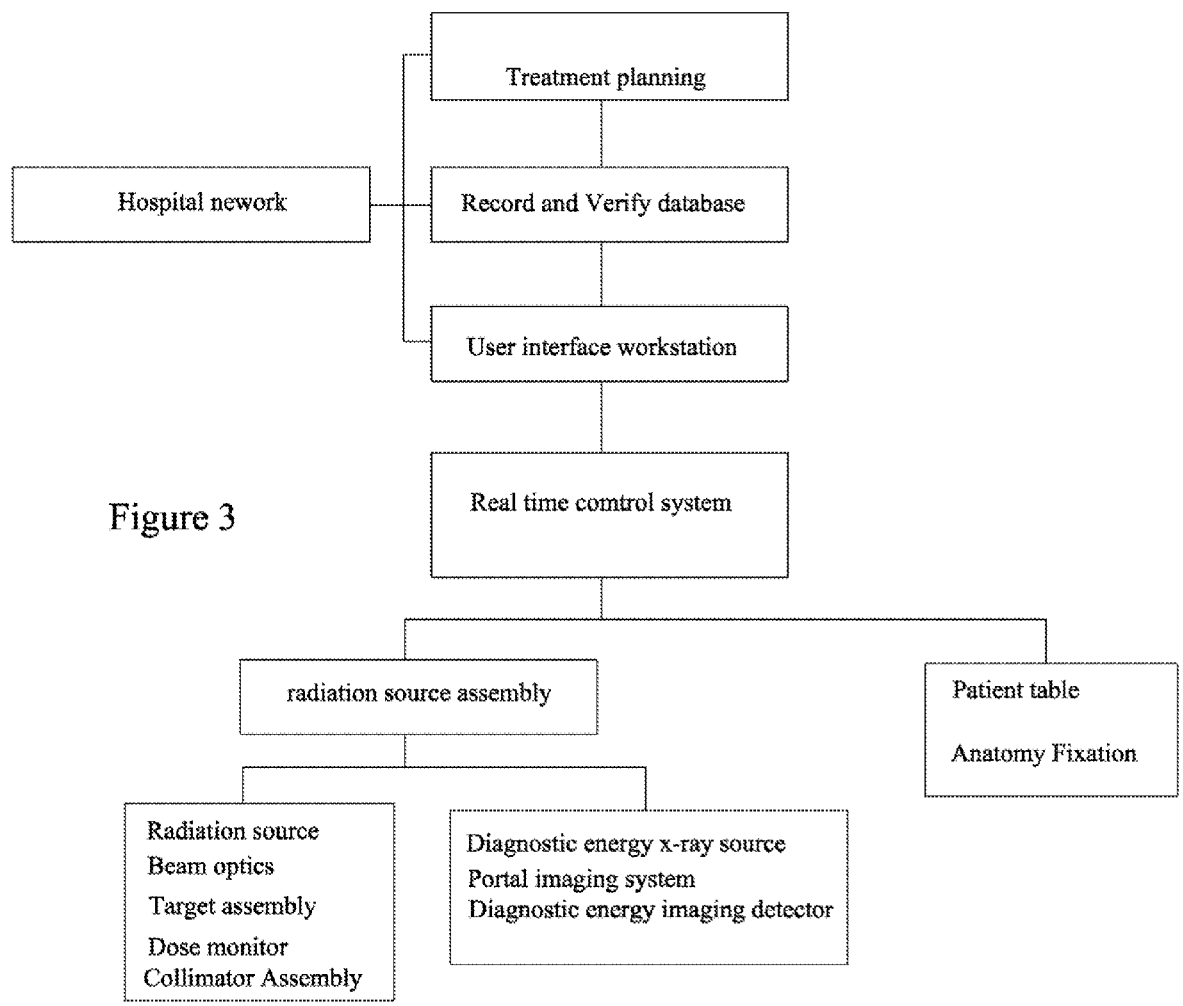
FIG. 3 is a block diagram of the present invention including an imaging system.

Referring to FIGS. 1A and 1B, a radiation therapy system of the present invention comprises a patient interface surface shown as a patient table 1 with an aperture 2 above a rotational assembly 3 carrying a radiation source 4 with beam shaping collimator 5, a diagnostic x-ray source 6, and an imaging detector 7, which can have a moveable position. An optional anatomy fixation device 8 holds the extremity of interest in a fixed position during the imaging and therapy phases of machine operation and is mounted to the patient interface surface. A beam block 9 (also referred to as a shielded base) intercepts unwanted energy from the primary beam of the radiation source 4 which escapes the treatment volume.

Figure 5:
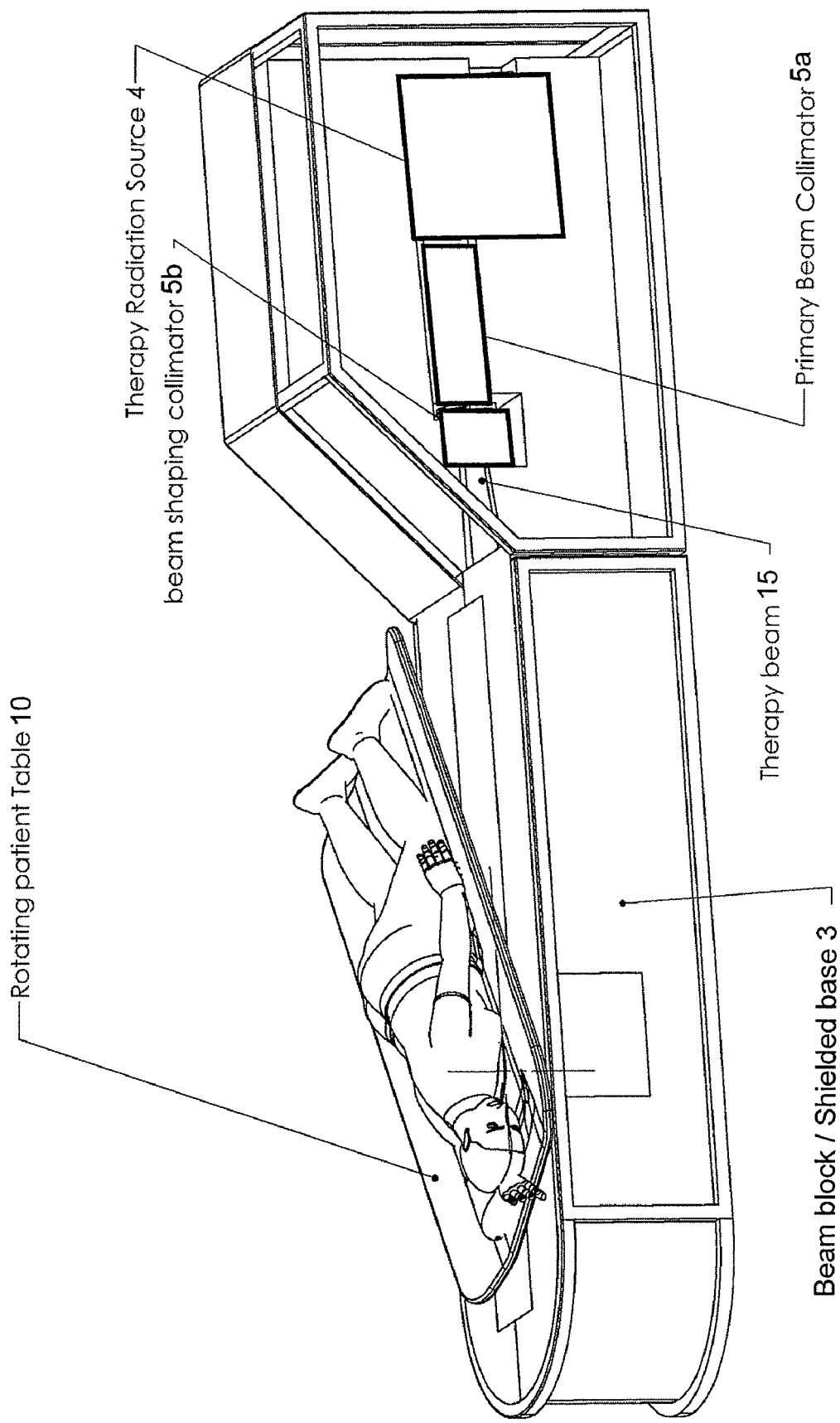
FIG. 5 is a fully shielded version of the therapy system with a rotating patient table.
Figures 6A, 6B:
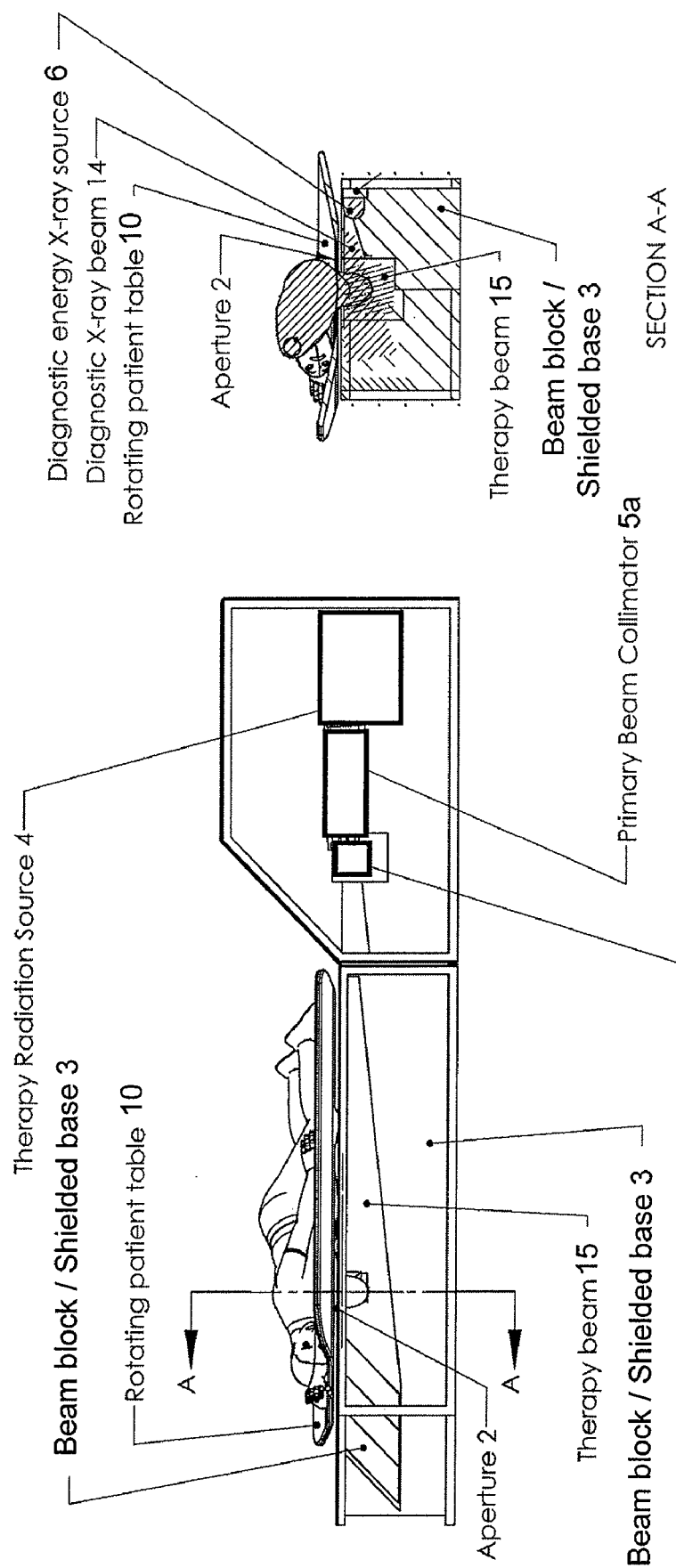
FIG. 6A is a side view of the therapy system shown in FIG. 5.
FIG. 6B is an end cross-sectional view of the therapy system shown in FIGS. 5 and 6A.
Figure 8:
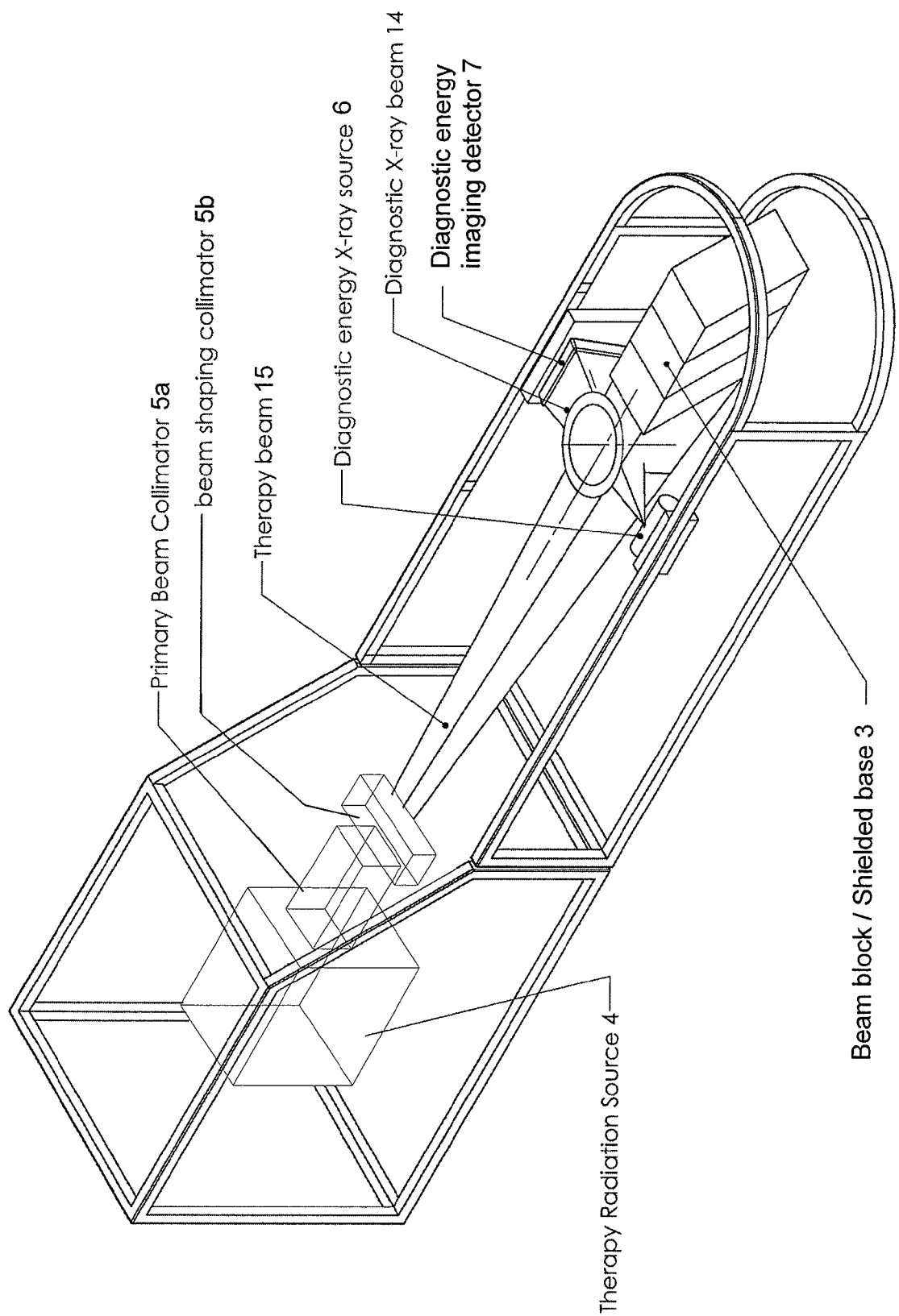
FIG. 8 is a perspective view of the shielded base shown FIGS. 5, 6A, 6B and 7.

Beam block 9 may include a portal imaging device which creates an image from the therapy beam passing through the treated anatomy. Positioning the rotational axis of the radiation source with respect to the anatomy is provided by either moving the source assembly relative to the table or the table relative to the source assembly. As can be appreciated by one of skill in the art, positioning the anatomy to be treated with respect to the therapy beam 6 is provided by either moving the table with respect to the rotational axis of the table or by selecting an offset portion of the beam by controlling the beam collimator 5. A diagnostic energy x-ray source and imager can be incorporated into the shielded base. The shielded base 3 can encompass the entire radiation source assembly 4 as shown in FIG. 5, providing full shielding from the radiation sources 4 and 6. This optional construction feature would allow the system to work in a room without primary shielding (typically a concrete bunker with walls several feet thick) for the radiation source, decreasing the cost of the installation substantially. This embodiment of the invention could preferably employ a shielded rotating patient table 10, reducing the complexity and cost of the rotating system as shown in FIGS. 5, 6A, 6B, 7 and 8. The rotating patient table 10 can optionally be raised with respect to the fixed shielded base 3 for positioning the patient's anatomy with respect to the therapy beam 6. When the patient table 10 is lowered into the treatment position, the gap between the high radiation zone within the surrounding shielded base 3 and the rotating patient table 10 is shielded by one of several means such as a labyrinth seal or dense brushes or wipers. The shielded table can be provided with interchangeable shielded apertures to accommodate differing size and shape anatomical targets. As an alternative to the elevating table, a shielded door can be provided in the surrounding shielded base 3 for access to the patient during initial positioning. Either the fixed or rotating table versions of the fully shielded embodiment of the invention can be mounted in a mobile enclosure such as an over-the road trailer with extensible sides to accommodate the rotating parts of the invention during operation. When in the stow position, the moveable extensions of the trailer can be retracted for transport to another medical facility. The fully shielded nature of the device provides for flexibility in siting the invention on fixed or mobile applications. At least some of these features are encompassed by one or more of the appended claims.

Figure 4:
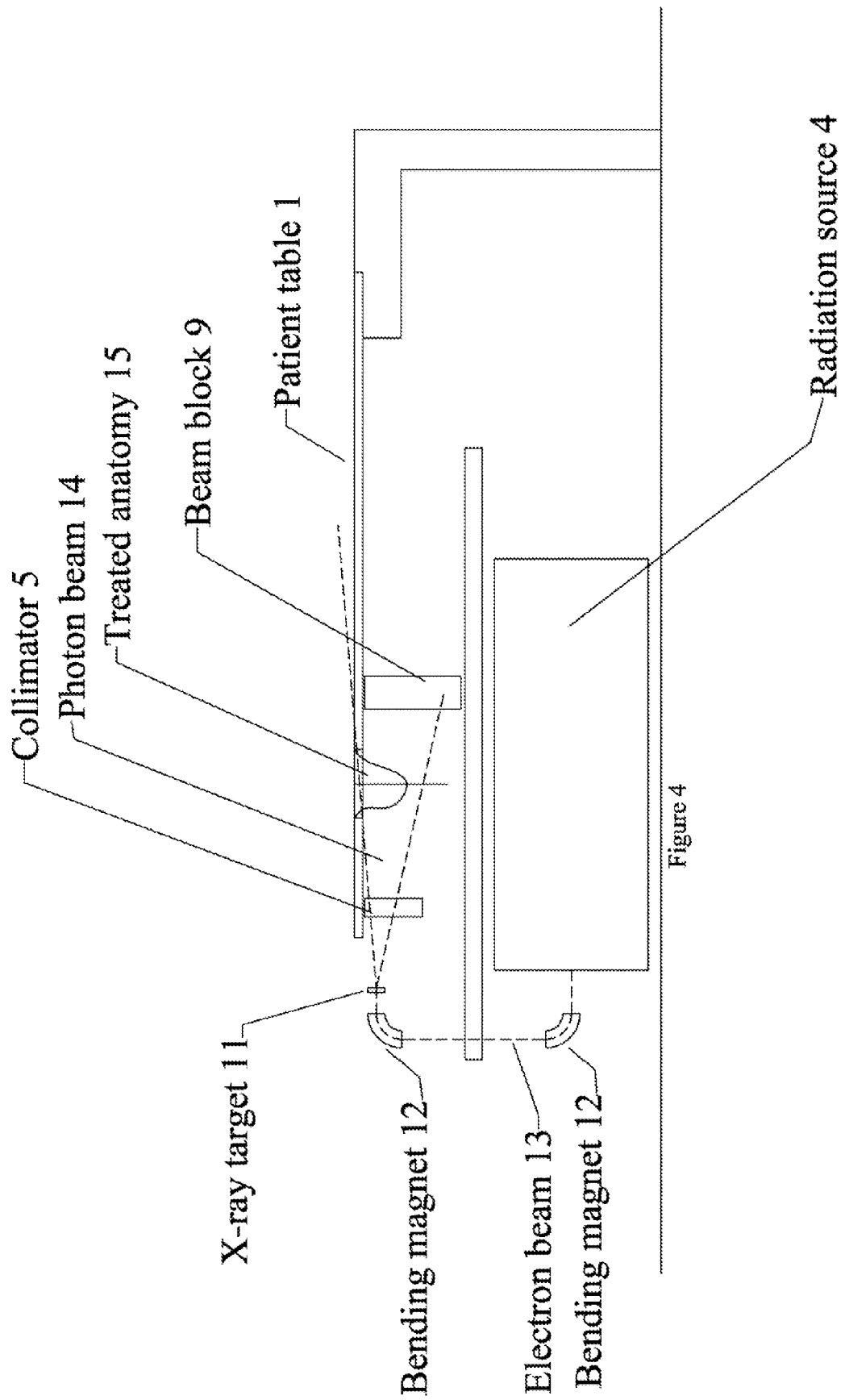
FIG. 4 is a plan cross-sectional view of a version of the system showing a fixed radiation source assembly employing bending magnets to enable folding the electron trajectory for a smaller device footprint.

In order to minimize the installed footprint of the system, it is possible to fold the electron beam trajectory as shown in FIG. 4. The LINAC radiation source 4 can be mounted horizontally below the patient table 1 and the electron beam 13 transported to the X-ray target 11 by employing bending magnets 12. If short enough, the LINAC radiation source 4 can also be mounted vertically in a position along the axis shown between bending magnets 12, allowing the use of only one bending magnet 12. Each of these mounting arrangements has positive and negative implications for the overall system design including overall size, servicing ease and radiation shielding requirements. By employing a bending magnet 12 it may be possible to get the electron beam axis closer to the bottom of the patient table 1 before it strikes the X-ray target 11, allowing better therapy photon beam 14 trajectories for treating anatomical targets closer to the patient table 1 bottom surface. FIG. 4 does not illustrate the fully shielded with rotating shielded patient table version of the invention for clarity, but the fully shielded rotating shielded patient table version is fully contemplated by this description. Many variations and combinations of the main elements of the invention are possible.

What is claimed is:

1. A radiation therapy system comprising:
a megavoltage radiation source and beam modulator producing a programmable radiation beam;

a rotatable patient positioning system, comprising:
  a patient interface surface; and
  an aperture to permit passage of the anatomy to be treated through the patient interface surface;
means to move the patient positioning system about a substantially vertical axis with respect to said radiation source;
a beam stop to substantially absorb the radiation beam which bypasses or is transmitted through the patient during operation;
an integrated shielding system cooperating with the patient interface surface configured to shield the patient, except for the anatomy to be treated, from substantially all direct and scattered radiation from the radiation source, beam modulator, and beam stop.

2. The radiation therapy system of claim 1 further including x-ray imaging means for visualizing the patient anatomy.

3. The radiation therapy system of claim 1 where the system is mounted in a mobile enclosure.

4. The radiation therapy system of claim 1 including a shielded enclosure which encloses the radiation source and modulator where the patient interface surface cooperates with the enclosure to shield the patient, except for the anatomy to be treated, from substantially all direct and scattered radiation from the radiation source, modulator and beam stop.

5. The radiation therapy system of claim 1 where said radiation source is a linear accelerator.

6. The radiation therapy system of claim 1 where the anatomy to be treated is a breast.

* * * * *